United States Patent [19]

Misaki et al.

[11] 4,202,966
[45] May 13, 1980

[54] GLUCAN POLYSACCHARIDE

[75] Inventors: Akira Misaki, 5-21, Kanno-cho, Nishinomiya-shi, Hyogo, Japan; Shigeo Takaya, Shizuoka, Japan; Koji Yokobayashi, Okayama, Japan; Yoichi Tsuburaya, Sakai, Japan

[73] Assignees: Director-Gen. of the Tea Experiment Station, Ministry of Agriculture and Forestry Japanese Government, Shizuoka; Akira Misaki, Hyogo; Kabushiki Kaisha Hayashibara Seibutsu Kagaku Kenkyujo, Okayama, all of Japan

[21] Appl. No.: 864,015

[22] Filed: Dec. 23, 1977

[30] Foreign Application Priority Data

Dec. 31, 1976 [JP] Japan .................................. 51-157935

[51] Int. Cl.² ............................................ C08B 37/00
[52] U.S. Cl. ............................................ 536/1; 264/7; 536/120; 435/101
[58] Field of Search ............................................ 536/1

[56] References Cited

U.S. PATENT DOCUMENTS

| | | | |
|---|---|---|---|
| 3,705,039 | 12/1972 | Matsuhashi et al. | 536/1 |
| 3,856,775 | 12/1974 | Fukuoka et al. | 536/1 |
| 4,029,886 | 6/1977 | Nakashio et al. | 536/1 |
| 4,036,920 | 7/1977 | Chihior et al. | 536/1 |

*Primary Examiner*—Johnnie R. Brown
*Attorney, Agent, or Firm*—Browdy and Neimark

[57] ABSTRACT

A glucan which is characterized by repeating units of [3)-Glc-(1→4)-Glc-(1→4)-Glc-(1→] wherein Glc represents alpha-D-glucopyranose residue. This glucan may be prepared by cultivating a microorganism of the genus Elsinoe capable of producing this glucan on a nutrient medium to produce this glucan and separating and recovering this glucan. This glucan may be used, for example, in the form of a film for packaging film material.

1 Claim, 2 Drawing Figures

GLUCAN POLYSACCHARIDE

FIELD OF THE INVENTION

The present invention relates to a glucan (elsinan) comprising repeating units of [3)-Glc-(1→4)-Glc-(1→4)-Glc-(1→] (wherein Glc hereinafter represents alpha-D-glucopyranose residue) and a process for the production thereof.

BACKGROUND OF THE INVENTION

The known polysaccharides comprising alpha-linked D-glucose, namely, alpha-glucan, include starch derived from plants, glycogen derived from animals, microbial dextran and microbia pullulan.

Although these alpha-glucans have been consumed in large amounts, their uses have been mainly directed to the food and pharmaceutical industries.

SUMMARY OF THE INVENTION

The object of the present invention is to develop a new glucan which is utilizable not only in the food and pharmaceutical industires but also in other various industrial fields. The present inventors discovered that the polysaccharide, obtained by cultivating microorganisms of genus Elsinoe on a nutrient medium, is a novel water-soluble glucan comprising repeating units of [3)-Glc-(1→4)-Glc-(1→4)-Glc-(1→] and has a number of industrial applications including those as various types of film. The inventors designated the novel glucan as elsinan.

DETAILED DESCRIPTION OF PREFERRED EMBODIMENTS

The elsinan of the present invention was identified as alpha-glucan, based on the following properties.

Purity: No contaminants were detactable on subjection to ultracentrifugation and electrophoresis.

Element analysis: Measurements; C=43.7 %, H=6.16 %, N<0.1 %, Ash<0.01 %, Calculations; C=44.4 %, H=6.17 %

Specific rotation; $[\alpha]_D^{25} +175 \sim 280°$ (l=1, c=1.6, 0.5N-NaOH)

Solubility: Dissolves readily in water, 0.1N-NaOH, 90 % formic acid, formamide, or dimethyl sulfoxide. Insoluble in organic solvents such as methanol, ethanol, acetone, chloroform, or ethyl acetate.

Appearance: A white, fine powder without taste or order.

Color reactions: Becomes green by the anthrone-sulfuric reaction. Becomes yellow by the cystein-sulfuric acid reaction. Remains colorless by the Morgan-Elson reaction. Iodine stain, negative.

Figure 1:
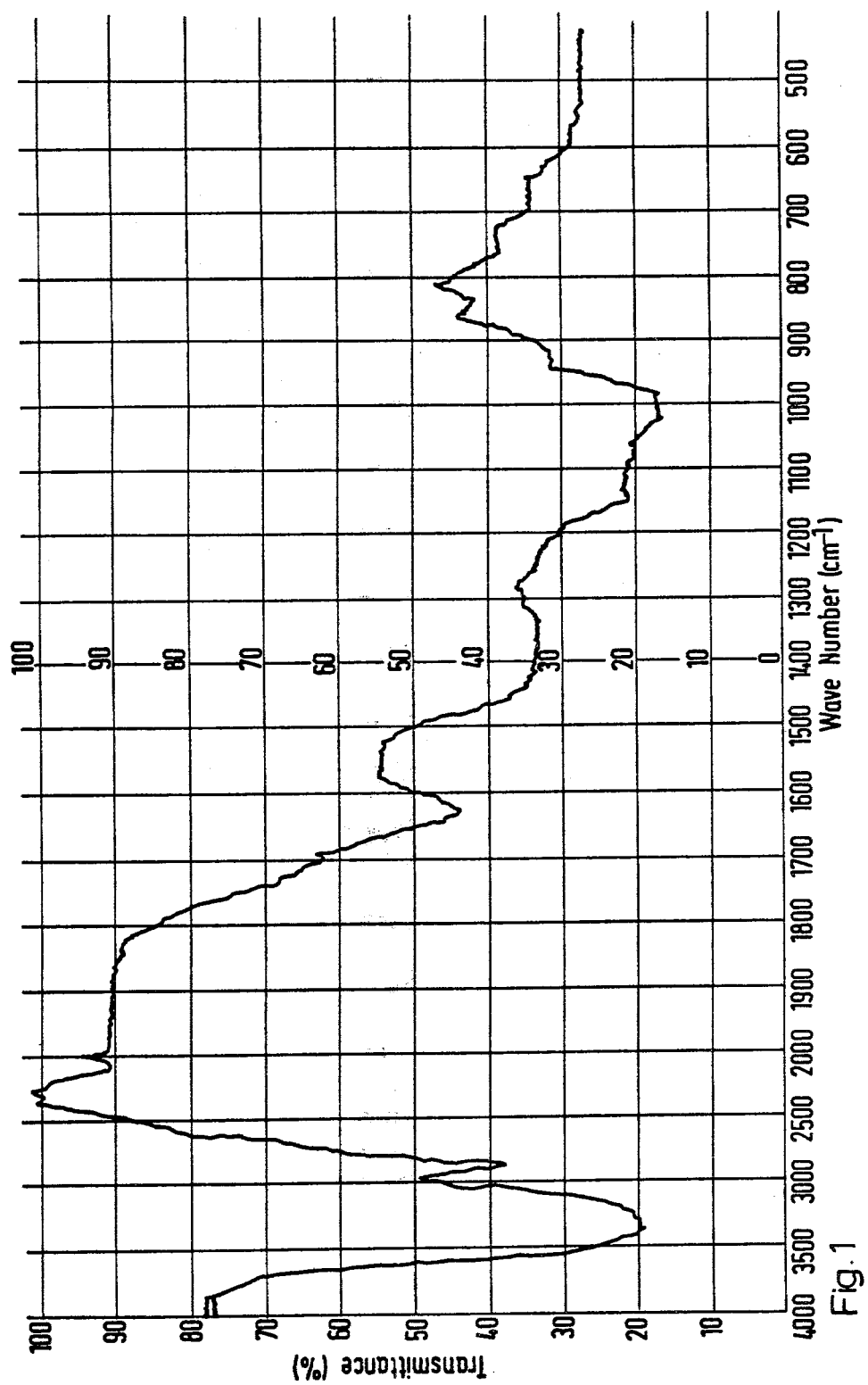
FIG. 1 shows the infrared spectrum of the purified elsinan.

Infrared spectrum: Infrared spectrum by the KBr tablet is given in FIG. 1. The absorbance at 840 cm$^{-1}$ in the infrared spectrum was characteristic of the alpha-type linkage.

Components: The analytical results obtained by paper chromatography, gas chromatography, liquid chromatography and glucose oxidase peroxidase method showed that the sugar obtained from hydrolyzing elsinan with 1N-sulfuric acid, 1N-hydrochloric acid or 1N-trichloroacetic acid was D-glucose.

In addition, the analytical results obtained by using chemical procedures such as methylation, periodate oxidation, Smith degradation and controlled Smith degradation show that the elsinan disclosed in the present invention is a novel glucan with an entirely new structure so far unknown. The novel glucan (elsinan) will be disclosed in further details.

(1) The high specific rotation, $[\alpha]_D^{25} +175 \sim 280°$, and the absorbance at 840 cm$^{-1}$ in the infrared spectrum indicate that all or most of the glucosidic linkages constructing elsinan are of alpha type.

(2) a. Qualitative and quantative analyses by gas chromatography and mass spectrum of the hydrolyzate of methylated elsinan show that the major components are 2,4,6-tri-O-methyl-D-glucose (ca. 30 %) and 2,3,6-tri-O-methyl-D-glucose (ca. 68 %), with small amounts of 2,4-di-O-methyl-D-glucose (ca. 1 %) and 2,3,4,6-tetra-O-methyl-D-glucose (ca. 1 %) present.

b. Complete oxidation of elsinan with periodate shows that 0.8 moles of periodate is consumed per glucose residue, with simultaneous formation of 0.07 moles of formic acid per glucose residue.

c. Qualitative and quantative analyses by paper chromatography, gas chromatography and liquid chromatography of the Smith degradation products of elsinan confirm that D-erythritol, 68~70 %, D-glucose, 29~30 %, glycerol, a trace.

The above results confirm that the glucose residues present in elsinan are essentially linear molecules comprising mainly alpha-1,4 and alpha-1,3 linkages in the moler ratio of 2.0~2.3 : 1.0.

A very few of the glucose residues linked at the C-1 and C-3 positions with the adjacent glucose residues are branched at the C-6 position by alpha-1,6 linkage. Such glucose residue are, at most, one out of every 70 glucose residues.

(3) The analyses by paper chromatography and gas chromatography of controlled Smith degradation products of elsinan indicate that D-erythritol and 2-O-alpha-D-glucopyranosyl-D-erythritol are, present in the molar ratio of 1.0~1.3 : 1.0 (the presence of 2-O-alpha-D-glucopyranosyl-D-erythritol indicates that the glucose residue is linked at the C-3 position by alpha-1,3-linkage with one adjacent glucose residue, and linked at the C-1 position by alpha-1,4 linkage with the adjacent glucose residue on the other side). In addition, a trace amount of glycerol derived from the non-reducing terminal glucose residue is detected.

(4) Partial hydrolysis of elsinan with dilute acid demonstrates that maltotriose, a small amount of maltotetraose, and the other trisaccharides and tetrasaccharides containing both alpha-1,4 and alpha-1,3 linkages are present in the hydrolyzate.

The above observations, (1), (2), (3) and (4), show that the elsinan disclosed in the invention is a polysaccharide which is hardly branched and which comprises alpha-1,3 and alpha-1,4 linkages, with the main structure in which approx. three alpha-1,4 linked-glucose residues are repeatedly linked in alpha-1,3 fashion. In other words, the elsinan has an essentially linear-chain structure wherein maltotriose units are linked repeatedly in alpha-1,3 fashion. The observatons, (2), (3) and (4), also show that although repeating units are predominantly maltotriose, maltotetraose residue is present in a small amount.

Consequently, elsinan is a novel glucan comprising repeating units of [3) -Glc-(1→4)-Glc-(1→4)-Glc-(1→]. The structure of elsinan can be illustrated as below.

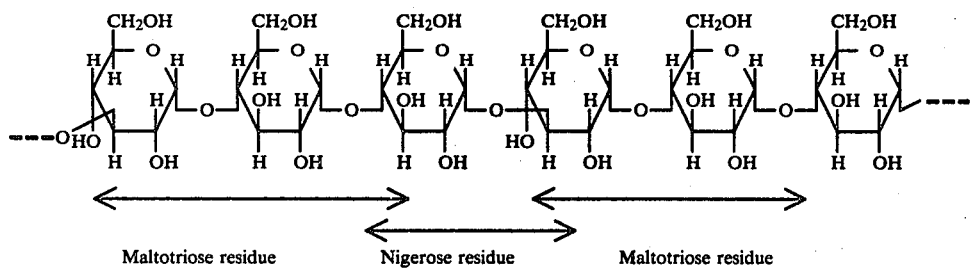

Maltotriose residue    Nigerose residue    Maltotriose residue

The mean molecular weight of elsinan is freely adjustable in the range of approx. 5,000 to approx. 10,000,000, because the glucan is producible by either chemical or biochemical procedure and is easily hydrolyzable with hydrochloric acid, sulfuric acid, etc.

The elsinan disclosed in the invention is chemically producible, for example, by polymerizing maltotriose units by repeating alpha-1,3 linkages.

The biochemical production of the elsinan disclosed in the invention is also attainable by utilizing microorganisms of genus Elsinoe.

For example, *Elsinoe leucospila* is employable for the effective production of the elsinan. The microorganism was reported by Jenkins A. E. et al. in *Arq. Inst. Biol. S. Paulo*, no. 17, pp. 67–72 (1946) and by Shigeo Takaya, et al. in *Study of Tea*, no. 49, pp. 7–88 (1975) and deposited by the present inventors to the Fermentation Institute, Agency of Industrial Science and Technology, 8-1-1, 5-chrome, Inagehigashi, Chiba, Japan, as FERM-P No. 3874.

The following microorganisms of genus Elsinoe are also employable for the production of elsinan:

| | |
|---|---|
| *Elsinoe ampelina* | IFO 5263, IFO 6359 |
| *Elsinoe araliae* | IFO 6166, IFO 7162 |
| *Elsinoe fawcetti* | IFO 6442, IFO 8417, ATCC 13200 |
| *Elsinoe annonae* | ATCC 15027 |
| *Elsinoe corni* | ATCC 11189 |
| *Elsinoe heveae* | ATTC 12570 |
| *Elsinoe lepagei* | ATCC 13008 |
| *Elsinoe tiliae* | ATCC 24510 |

The process for producing elsinan will be described in further details. The above-mentioned microorganisms of the genus Elsinoe are cultivated on a culture medium containing suitable carbon sources, nitrogen sources, minerals and other nutrients necessary for producing elsinan, and then the resulting glucan is separated and recovered.

A culture medium may be in solid or liquid form. In the case of liquid medium, although static culture is also feasible, shaking culture or submerged culture results in a higher yeild of elsinan.

Potato extract with hot water, and sucrose are suitablefor culture medium. Synthetic compounds such as nitrates, ammonium salts, urea, and natural organic substances such as polypeptone, corn steep liquor, yeast extract, defatted soybean extract, peptides, amino acids may be used freely as nitrogen sources.

Phosphates, potassium salts, sulfates, and magnesium salts may be used freely as minerals. If necessary, other minerals such as ferrites or ferrates, calcium salts and manganates are also employable.

The initial pH of the culture medium should be in the range that favors microbial growth and elsinan production. Generally, pH 5–8 is preferable. Similarly, the cultivation temperature should be in the range that favors the microbial growth and elsinan production. Generally, 20–30°C. is preferable. Cultivation is carried out until a maximum yield of elsinan is obtained, generally, 3–7 days.

The resultant cultural broth wherein elsinan is produced and accumulated in accordance with the above-mentioned procedure exhibits high viscosity. The broth is treated by suitable procedures such as filtration or centrifugation to remove the cells and mycelia, and the elsinan in the thus-obtained clear filtrate or supernatant precipitates in a white plumage or gum form by the addition of appropriate precipitants, for example, organic precipitants such as methanol, ethanol, isopropanol and acetone. The elsinan is recovered by suitable procedures such as filtration or centrifugation. The resultant elsinan as such may be used as the finished product, or the elsinan may be used after further purification by dissolving in water and efffecting precipitation repeatedly by the addition of organic precipitants and, if necessary, drying. Any procedures such as through flow drying, hot air drying, spray drying, drum drying, vacuum drying and lyophylizing are applicable for the drying.

The process for producing elsinan is illustrated by the following example which is not intended to restrict the invention. Example:

A liquid medium consisting of 5 w/v % sucrose, 0.5 w/v % yeast extract, 0.042 w/v % $Na_2 HPO_4$, 0.018 w/v % $KH_2 PO_4$, semi-permeable-membrane-permeated solution of potato extract with hot water (300 g. fresh potato was used per one liter medium.) and water was sterilized at 120°C. for 20 minutes, and then cooled. Thereafter, the medium was inoculated with *Elsinoe leucospila*, FERM-P No. 3874, at an initial pH of 6.8, and subjected to submerged culture at 24°C. for five days. After pasteurizing the resultant broth at 85°C. for 15 minutes, the cells and mycelia were removed therefrom by centrifugation (5,000 g. for 20 minutes). With the addition of 1.5 volumes ethanol to the thus-obtained clear supernatant, crude elsinan was obtained as a precipitate in a plumage or gum form. The crude elsinan was dissolved in water and subjected to centrifugation to remove insoluble substances, as described above, and then precipitation was effected by adding, ethanol again to the supernatant. After the procedure was repeated three times, the precipitate was lyophilized. White powder of purified elsinan was obtained at an approx. 30 % yield against the sucrose used in the medium.

Figure 2:
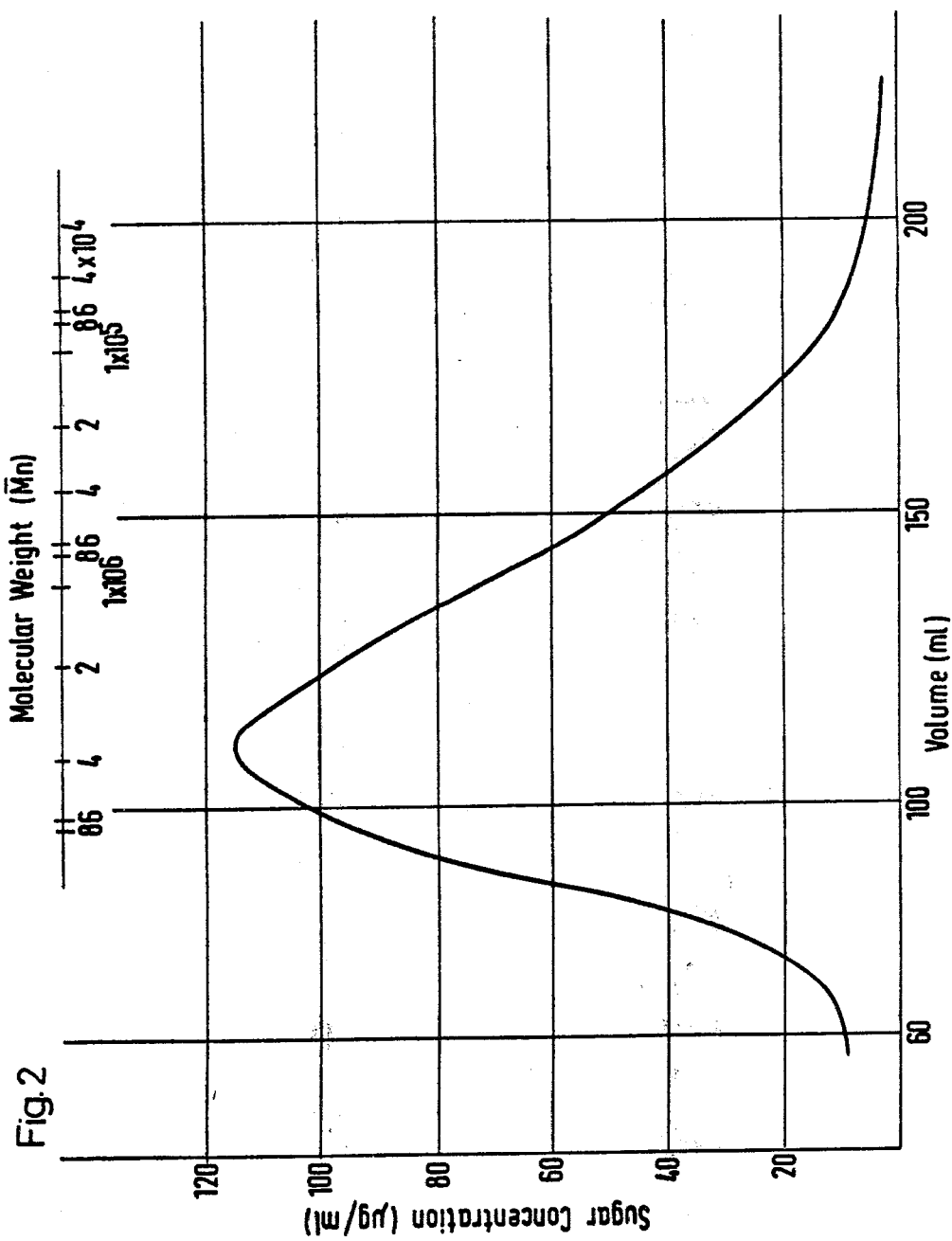
FIG. 2 shows the molecular weight distribution of the purified elsinan by the gel filtration method.

The viscosity of a 3 w/w % aqueous solution of the purified elsinan determined at 30°C., using Brookfield rotational viscometer, was 407 cps. The estimation of molecular weight distribution of the purified elsinan by the gel filtration method gave a distribution range from approx. 10,000 to approx. 10,000,000 or more, as illustrated in FIG. 2.

A 5 w/w % aqueous solution of the purified elsinan was casted uniformly on a clear glass plate and air-dried. A colorless, clear, intensive, flexible and self-supporting film was formed. The excellent film formability of elsinan leads to the applications as packaging film material and coating agent.

What is claimed is:

1. A glucan (elsinan) comsisting predominantly of repeating units of [3)-Glc-(1→4)-Glc-(1→4)-Glc-(1→] (wherein Glc represents alpha-D-glucopyranose residue), said glucan having a molecular weight of approximately 5,000 to approximately 10,000,000.